United States Patent [19]
Yuasa et al.

[11] Patent Number: 5,942,629
[45] Date of Patent: Aug. 24, 1999

[54] PROCESS FOR PRODUCING OPTICALLY ACTIVE PYRROLIDINE DERIVATIVES

[75] Inventors: Yoshifumi Yuasa; Tsukasa Sotoguchi; Nobuo Seido, all of Kanagawa, Japan

[73] Assignee: Takasago International Corporation, Tokyo, Japan

[21] Appl. No.: 08/976,491

[22] Filed: Nov. 24, 1997

[30] Foreign Application Priority Data

Jan. 24, 1997 [JP] Japan ............................... 9-024514

[51] Int. Cl.⁶ .................................................. G07D 207/09
[52] U.S. Cl. ....................................................... 548/566
[58] Field of Search ............................................. 548/566

[56] References Cited

U.S. PATENT DOCUMENTS 5,461,165  10/1995  Domagala et al. ..................... 548/566

FOREIGN PATENT DOCUMENTS 0295890  12/1988  European Pat. Off. .
94/26708  11/1994  WIPO .

OTHER PUBLICATIONS

Chemical Abstracts, vol. 121, No. 9, Aug. 29, 1994, Abstract No. 108503x, p. 1044; XPOO2063630 and JP 00 672 999 A (Fujisawa Pharm Co.), pp. 1057–1061.

Schoeder, M.C., et al., "Synthesis of the Four Stereoisomers of Several 3–(1–Aminoethyl) Pyrrolidines. Important Intermediates In the Preparation of Quinolone Antibacterials" Journal of Heterocyclic Chemistry vol. 29, No. 6, Oct. 1992, pp. 1481–1498, XP00064751.

Y.Kimura; "Synthesis And Structure—Activity Relationships of 7–3–1–Aminocycloalkyl) Pyrrolidinyl!–Quino Lone Antibacterials", Chemical Pharmaceutical Bulletin, vol. 42, No. 7, 1994, XP002063628; pp. 1442–1454.

J.S. Plummer, et al., "Stereoelective Michael Additions of Nitromethane Yielding 3R (IS N–Substituted Aminoethyl) Pyrrolidines" Tetrahedron Letters, vol. 34, No. 47, 1993, pp. 7529–7532.

Primary Examiner—Mukund J. Shah
Assistant Examiner—Ann M. Kessinger
Attorney, Agent, or Firm—Sughrue, Mion, Zinn, Macpeak & Seas, PLLC

[57] ABSTRACT

A production process for obtaining optically active (3R,1'S)-1-benzyl-3-[(1'-N-methylamino)ethyl]pyrrolidine or (3R, 1'S)-3-[(1'-N-methylamino)ethyl]pyrrolidine used as an intermediate for the synthesis of pharmaceutical preparations such as anti-fungal agents in high purity and in high yield using a reduced number of processing steps. The process comprises asymmetrically hydrogenating 3-acetyl-1-benzyl-2-pyrrolidinone in the presence of a complex formed from bidentate phosphine and ruthenium as a catalyst to provide (3S,1'R)-1-benzyl-3-[(1'-hydroxy)ethyl]-2-pyrrolidinone, then reducing with a hydride to provide (3R,1'R)-1-benzyl-3-[(1'-hydroxy)ethyl]pyrrolidine, mesylating or tosylating to provide (3R,1'R)-1-benzyl-3-[(1'-methanesulfonyloxy)ethyl]pyrrolidine or (3R,1'R)-1-benzyl-3-[(1'-p-toluenesulfonyloxy)ethyl]pyrrolidine, and reacting with methylamine to obtain (3R,1'S)-1-benzyl-3-[(1'-N-methylamino)ethyl]pyrrolidine. The prcess may further comprise de-benzylating (3R,1'S)-1-benzyl-3-[(1'-N-methylamino)ethyl]pyrrolidine to obtain (3R,1'S)-3-[(1'-N-methylamino)ethyl]pyrrolidine.

8 Claims, 3 Drawing Sheets

PROCESS FOR PRODUCING OPTICALLY ACTIVE PYRROLIDINE DERIVATIVES

BACKGROUND OF THE INVENTION

1. Field of the Invention

The present invention relates to a process for producing (3R,1'S)-1-benzyl-3-[(1'-N-methylamino)ethyl]pyrrolidine or (3R,1'S)-3-[(1'-N-methylamino)ethyl]pyrrolidine as an intermediate for the synthesis of quinolone type anti-fungal agents such as norfloxacin, ciprofloxacin, etc.

2. Description of the Prior Art

As shown in WO 9426708, a conventional process for producing (3R,1'S)-3-[(1'-N-methylamino)ethyl]pyrrolidine (14) involves subjecting optically active phenylethylamine as a starting material to formylation followed by the steps of monomethylation by reduction, addition reaction of crotonate, de-benzylation, conversion into β-lactam by allylation and ring closure, ozone oxidation, reduction with sodium borohydride, mesylation, reaction with benzylamine, formation of a pyrrolidinone ring by a ring-enlarging reaction under heating and subsequent reduction with lithium aluminum hydride, and finally de-benzylation to obtain (3R,1'S)-3-[(1'-N-methylamino)ethyl]pyrrolidine as a final product (see FIG. 2).

An alternative method, as described in *Tetrahedron Letters*, 34:7529 (1993), involves subjecting L-alanine as a starting material to t-butoxycarbonylation (conversion into BOC) followed by the steps of conversion into a β-ketoester by elongation of the carbon chain, reduction of the carbonyl group, mesylation, conversion into an unsaturated ester by 1,8-diazobicyclo[5,4,0]undeca-7-ene (DBU), addition of nitromethane, formation of a pyrrolidinone ring by reduction and ring closure with Raney nickel, and finally reduction with lithium aluminum hydride to obtain (3R,1'S)-3-[(1'-N-methylamino)ethyl]pyrrolidine (see FIG. 3).

Furthermore, a method of preparing racemates is described in *Chemical Pharmaceutical Bulletin Japan*, 42: 1442 (1994) and Japanese Patent Application Laid-open Nos. 60-139830 and 279991/85, in which 4-carboxy-N-benzyl-2-pyrrolidone is acetylated and converted into an oxime, and the oxime is reduced and converted into BOC which is finally reduced with lithium aluminum hydride to obtain 3-[(1'-N-methylamino)ethyl]pyrrolidine.

These methods are not industrially adequate due to the need for many steps and complicated procedures, and because expensive reagents and optically active materials are used therein.

SUMMARY OF THE INVENTION

Therefore, it is an object of the present invention to provide a safe and easy process for producing optically active (3R,1'S)-1-benzyl-3-[(1'-N-methylamino)ethyl] pyrrolidine or (3R,1'S)-3-[(1'-N-methylamino)ethyl] pyrrolidine used as an intermediate for the synthesis of pharmaceutical preparations such as anti-fungal agents.

As a result of their diligent study in view of the above problems of the prior art, the present inventors discovered a production process which comprises subjecting 3-acetyl-1-benzyl-2-pyrrolidinone (1) to asymmetric hydrogenation using a complex formed from bidentate phosphine and ruthenium as a catalyst to produce (3S,1'R)-1-benzyl-3-[(1'-hydroxy)ethyl]-2-pyrrolidinone (2) of high purity in high yield, then reducing (2) with sodium borohydride and sulfuric acid or lithium aluminum hydride to provide (3R,1'R)-1-benzyl-3-[(1'-hydroxy)ethyl]pyrrolidine (3), treating the resulting (3R,1'R)-1-benzyl-3-[(1'-hydroxy)ethyl] pyrrolidine (3) with methanesulfonyl chloride or p-toluenesulfonyl chloride in the presence of a base to provide (3R,1'R)-1-benzyl-3-[(1'-methanesulfonyloxy) ethyl]pyrrolidine (4a) or (3R,1'R)-1-benzyl-3-[(1'-p-toluenesulfonyloxy)ethyl]pyrrolidine (4b), and followed by reacting with methylamine to obtain (3R,1'S)-1-benzyl-3-[(1'-N-methylamino)ethyl]pyrrolidine (5). The resulting (3R,1'S)-1-benzyl-3-[(1'-N-methylamino)ethyl]pyrrolidine (5) may then be subjected to de-benzylation to obtain (3R,1'S)-3-[(1'-N-methylamino)ethyl]pyrrolidine (14). The entire process is carried out in a safe and easy manner. Thus, the present invention has been achieved based on the above findings.

That is, the present invention is as follows:

A process for producing (3R,1'S)-1-benzyl-3-[(1'-N-methylamino)ethyl]pyrrolidine represented by formula (5):

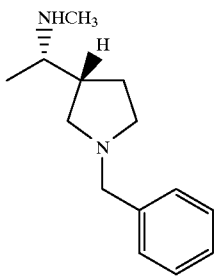

(5)

which comprises asymmetrically hydrogenating 3-acetyl-1-benzyl-2-pyrrolidinone represented by formula (1):

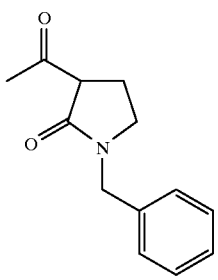

(1)

in the presence of a complex formed from bidentate phosphine and ruthenium as a catalyst to produce (3S,1'R)-1-benzyl-3-[(1'-hydroxy)ethyl]-2-pyrrolidinone represented by formula (2):

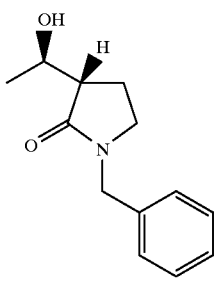

(2)

reducing the resulting (3R, 1'R)-1-benzyl-3-[(1'-hydroxy) ethyl]-2-pyrrolidinone to produce (3R,1'R)-1-benzyl-3-[(1'-hydroxy)ethyl]pyrrolidine represented by formula (3):

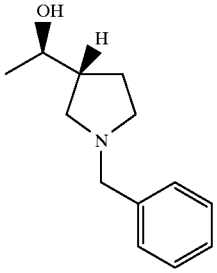

(3)

mesylating and/or tosylating the resulting (3R,1'R)-1-benzyl-3-[(1'-hydroxy)ethyl]pyrrolidine to produce (3R,1'R)-1-benzyl-3-[(1'-methanesulfonyloxy)ethyl]pyrrolidine and/or (3R,1'R)-1-benzyl-3-[(1'-p-toluenesulfonyloxy)ethyl]pyrrolidine represented by formula (4):

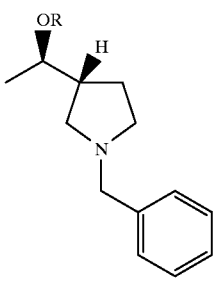

(4)

wherein R represents a methanesulfonyl group or a p-toluenesulfonyl group, and methylaminating the resulting (3R,1'R)-1-benzyl-3-[(1'-methanesulfonyloxy)ethyl] pyrrolidine or (3R,1'R)-1-benzyl-3-[(1'-p-toluenesulfonyloxy)ethyl]pyrrolidine.

The process for producing (3R,1'S)-1-benzyl-3-[(1'-N-methylamino)ethyl] pyrrolidine according to item 1 above, wherein the bidentate phosphine is a bidentate phosphine L represented by the following general formula (6):

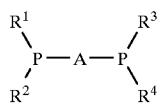

(6)

wherein $R^1$, $R^2$, $R^3$ and $R^4$ may be the same or different and each represents a phenyl group, a cyclohexyl group, a cyclopentyl group, a C1 to C4 lower alkyl group, a C1 to C4 lower alkoxy group or a halogen-substituted phenyl group;

A is represented by the following general formula (7):

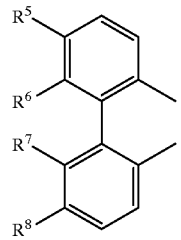

(7)

wherein $R^5$ and $R^8$ each represents a hydrogen atom and $R^6$ and $R^7$ each represents a methyl group, or $R^5$ and $R^6$ or $R^7$ and $R^8$ may combine to form a tetramethylene group, or A is represented by the following general formula (8):

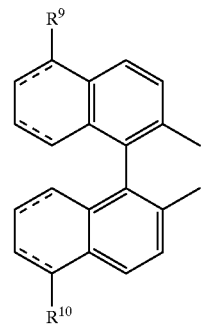

(8)

wherein $R^9$ and $R^{10}$ may be the same or different and each represents a hydrogen atom, an amino group, an acetylamino group or —$SO_3M$ where M represents a hydrogen atom or an alkali metal atom, and the broken line is a saturated or double bond.

The process for producing (3R,1'S)-1-benzyl-3-[(1'-N-methylamino)ethyl] pyrrolidine according to item 1 above, wherein the complex formed from bidentate phosphine and ruthenium is represented by the following general formula (9):

$$Ru_xH_yCl_z(L)_2(S)_p \quad (9)$$

wherein L is a bidentate phosphine represented by the following general formula (6):

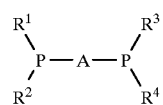

(6)

wherein $R^1$, $R^2$, $R^3$, $R^4$ and A have the same meanings as defined above, and S is represented by the following general formula (10):

$$NR^{11}R^{12}R^{13} \quad (10)$$

wherein $R^{11}$, $R^{12}$ and $R^{13}$ may be the same or different and each represents a lower alkyl group, and when y is 0, x is 2, z is 4 and p is 1; when y is 1, x is 1, z is 1 and p is 0.

The process for producing (3R,1'S)-1-benzyl-3-[(1'-N-methylamino)ethyl]pyrrolidine according to item 1 above, wherein the complex formed from bidentate phosphine and ruthenium is represented by the following general formula (11):

$$Ru(OCOR^{14})_2(L) \qquad (11)$$

wherein $R^{14}$ represents a C1 to C4 lower alkyl group or trifluoromethyl group, and L represents the same bidentate phosphine as defined above.

The process for producing (3R,1'S)-1-benzyl-3-[(1'-N-methylamino)ethyl]pyrrolidine according to item 1 above, wherein the complex formed from bidentate phosphine and ruthenium is a complex represented by the following general formula (12):

$$RuX_2(L) \qquad (12)$$

wherein X represents a halogen atom, and L represents the same bidentate phosphine as defined above.

The process for producing (3R,1'S)-1-benzyl-3-[(1'-N-methylamino)ethyl]pyrrolidine according to item 1 above, wherein the complex formed from bidentate phosphine and ruthenium is a complex represented by the following general formula (13):

$$RuX_kJ_m(L)Q_n \qquad (13)$$

wherein X represents a halogen atom, and J represents benzene, p-cymene, a C1 to C4 lower alkyl benzoate or acetonitrile, Q represents a halogen atom, $ClO_4$, $PF_6$ or $BF_4$, L represents the same bidentate phosphine as defined above; when J is benzene, p-cymene or a lower alkyl benzoate, m is 1 and n is 1 when k is 1; and when J is acetonitrile, m is 1 and n is 1 when k is 1, and m is 4 and n is 2 when k is 0.

The process for producing (3R,1'S)-1-benzyl-3-[(1'-N-methylamino)ethyl]pyrrolidine according to item 1 above, which comprises reducing (3S,1'R)-1-benzyl-3-[(1'-hydroxy)ethyl]-2-pyrrolidinone represented by formula (2) with lithium aluminum hydride, borane, sodium borohydride and a mineral acid or with sodium borohydride and an organic acid.

The process for producing (3R,1'S)-1-benzyl-3-[(1'-N-methylamino)ethyl]pyrrolidine according to item 1 above, which comprises reacting (3R,1'R)-1-benzyl-3-[(1'-hydroxy)ethyl]pyrrolidine represented by formula (3) with methanesulfonyl chloride or paratoluenesulfonyl chloride in the presence of a base.

The process for producing (3R,1'S)-1-benzyl-3-[(1'-N-methylamino)ethyl]pyrrolidine according to item 1 above, which comprises reacting (3R,1'R)-1-benzyl-3-[(1'-methanesulfonyloxy)ethyl]pyrrolidine and/or (3R,1'R)-1-benzyl-3-[(1'-paratoluenesulfonyloxy)ethyl]pyrrolidine represented by formula (4) with methylamine in an organic solvent.

PREFERRED EMBODIMENTS OF THE INVENTION

The present invention is described in detail below.

Figure 1:
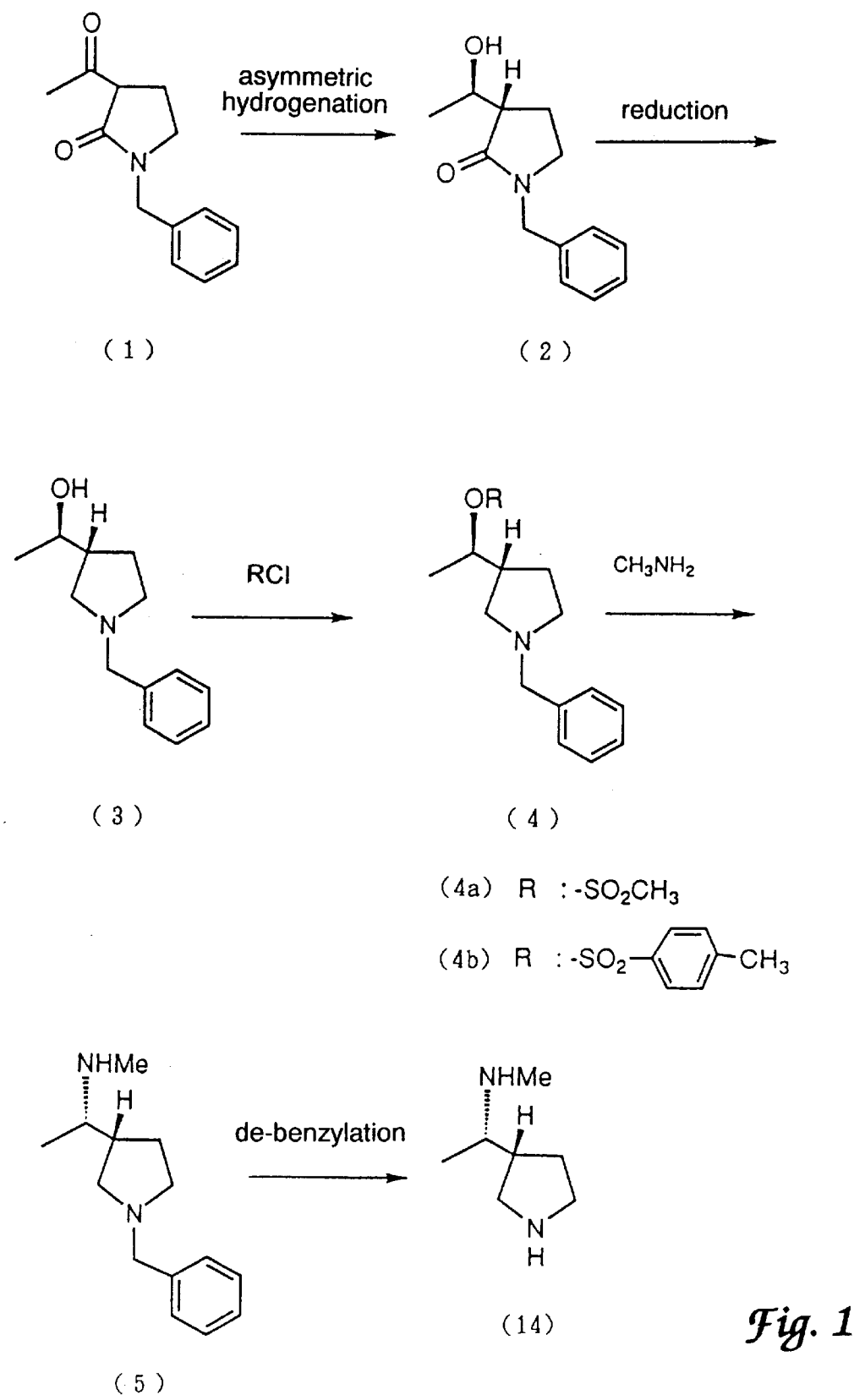
FIG. 1 shows a preferred process for preparing (3R,1'S)-1-benzyl-3-[(1'-N-methylamino)ethyl]pyrrolidine from 3-acetyl-1-benzyl-2-pyrrolidinone as a starting material.
Figure 2:
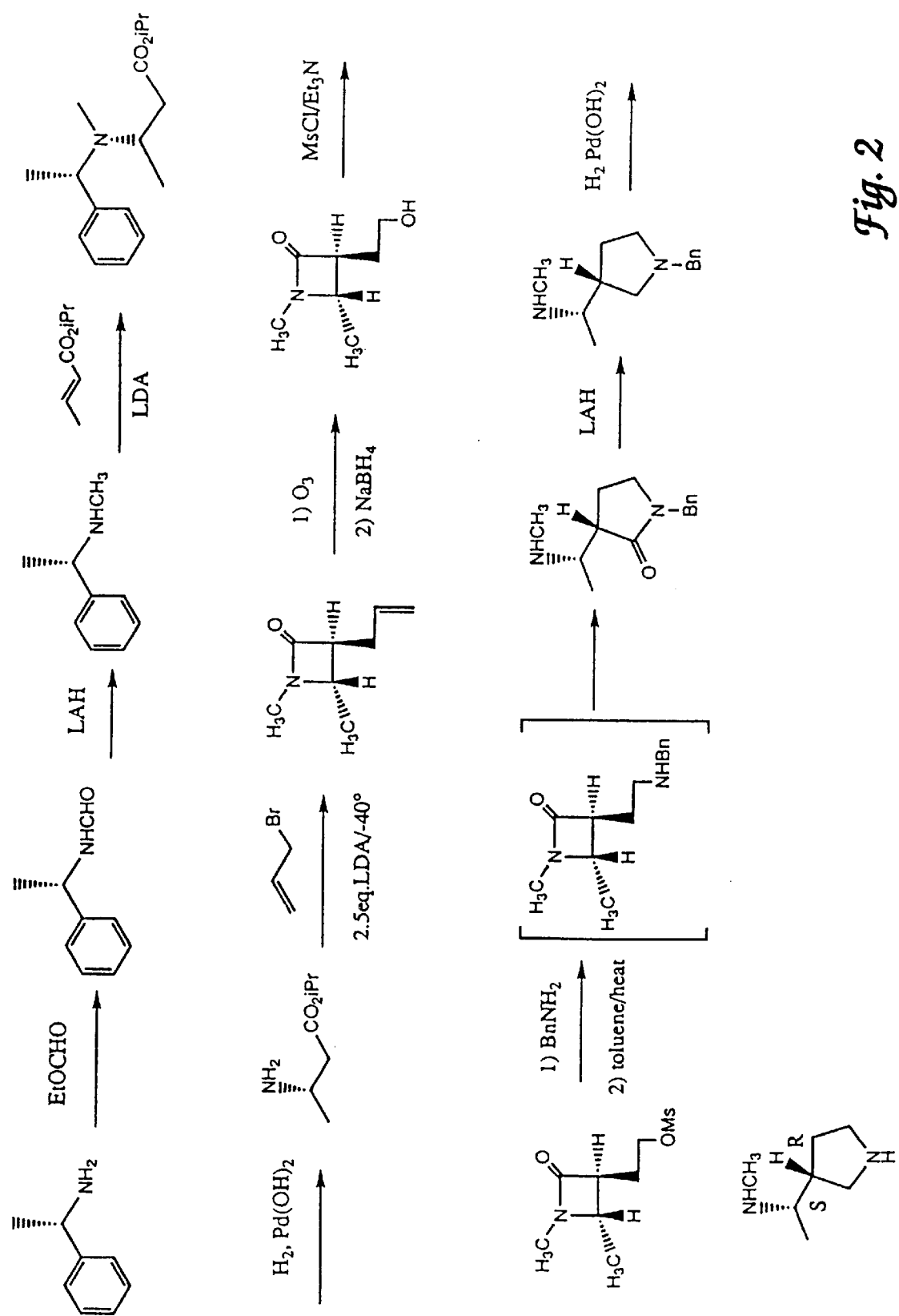
FIG. 2 shows a conventional process for preparing (3R, 1'S)-3-[(1'-N-methylamino) ethyl]pyrrolidine from optically active phenylethylamine as a starting material.
Figure 3:
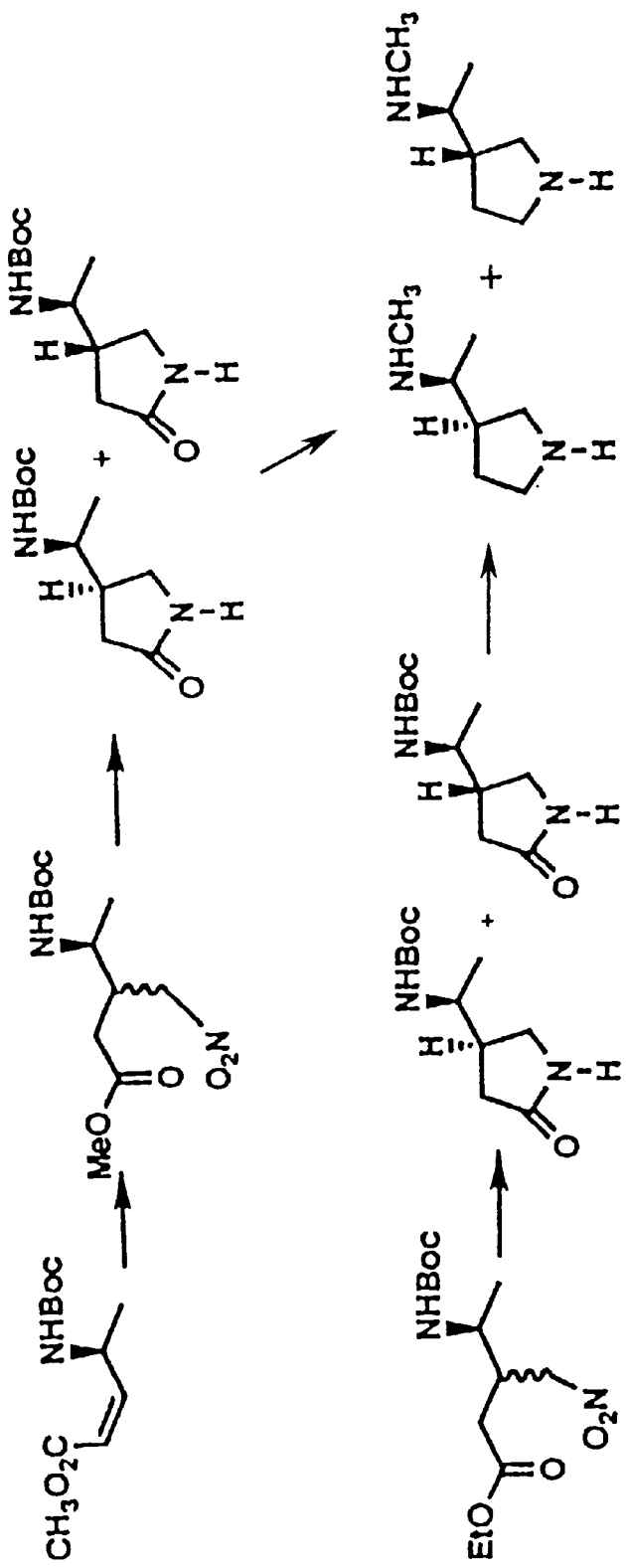
FIG. 3 shows a conventional process for preparing (3R, 1'S)-3-[(1'-N-methylamino) ethyl] pyrrolidine from L-alanine as a starting material.

A preferred process of the present invention in which (3R,1'S)-1-benzyl-3-[(1'-N-methylamino)ethyl]pyrrolidine (5) is obtained from 3-acetyl-1-benzyl-2-pyrrolidinone (1) as a starting material is shown in FIG. 1.

The starting material in the present invention, i.e. 3-acetyl-1-benzyl-2-pyrrolidinone (1) represented by formula (1), can be obtained, for example, by the method described in Japanese Patent Application Laid-Open No. 4-95067, that is, by reacting commercially available 1-benzyl-2-pyrrolidinone with dimethylacetamide at −60° C. in the presence of lithium di-isopropylamide.

One aspect of the present invention lies in producing (3S,1'R)-1-benzyl-3-[(1'-hydroxy)ethyl]-2-pyrrolidinone (2) by asymmetric hydrogenation of 3-acetyl-1-benzyl-2-pyrrolidinone represented by formula (1) in the presence of a complex formed from bidentate phosphine and ruthenium as a catalyst.

The complex formed from ruthenium and optically active phosphine used as the catalyst includes:

(i) A complex represented by the following general formula (9):

$$Ru_xH_yCl_2(L)_2(S)_p \qquad (9)$$

wherein L is bidentate phosphine represented by general formula (6):

(6)

wherein $R^1$, $R^2$, $R^3$, $R^4$ and A have the same meanings as defined above, and S is represented by the following general formula (10):

$$NR^{11}R^{12}R^{13} \qquad (10)$$

wherein $R^{11}$, $R^{12}$ and $R^{13}$ may be the same or different and each represents a C1 to C4 lower alkyl group, and when y is 0, x is 2, z is 4, and p is 1; when y is 1, x is 1, z is 1, and p is 0, (ii) A complex represented by the following general formula (11):

$$Ru(OCOR^{14})_2(L) \qquad (11)$$

wherein $R^{14}$ represents a C1 to C4 lower alkyl group or a trifluoromethyl group, and L represents the same bindentate phosphine as defined above, (iii) A complex represented by the following general formula (12):

$$RuX_2(L) \qquad (12)$$

wherein X represents a halogen atom, and L represents the same bidentate phosphine as defined above, and (iv) A complex represented by the following general formula (13):

$$RuX_kJ_m(L)Q_n \qquad (13)$$

wherein X represents a halogen atom, and J represents benzene, p-cymene, a C1 to C4 lower alkyl benzoate or acetonitrile, Q represents a halogen atom, $ClO_4$, $PF_6$ or $BF_4$, L represents the same bidentate phosphine as defined above; when J is benzene, p-cymene or a lower alkyl benzoate, m is 1 and n is 1 when k is 1; and when J is acetonitrile, m is 1 and n is 1 when k is 1, and m is 4 and n is 2 when k is 0.

The ruthenium compound used as the starting material for such complexes includes, e.g., $[RuCl_2(COD)]_n$ (where COD is 1,5-cyclooctadiene, n is an integer of 1 to about 1000), $[RuBr_2(COD)]_n$, $[RuCl_2(NBD)]_n$ (wherein NBD is norbornadiene), $[RuBr_2(NBD)]_n$, $[RuCl_2(benzene)]_2$, $(RuBr_2(benzene)]_2$, $[RuI_2(benzene)]_2$, $(RuCl_2(p\text{-cymene})]_2$, $(RuBr_2(p\text{-cymene})]_2$, $[RuI_2(p\text{-cymene})]_2$, etc.

The optically active bindentate phosphine as another starting material for the above complexes includes, e.g., the following compounds. A symbol for optical rotation, (+) or (−), is omitted for the following description of optically active bidentate phosphines.

2,2'-bis(diphenylphosphino)-6,6'-dimethylbiphenyl (referred to hereinafter as "biphemp"), 2,2'-bis(di(p-tolyl)phosphino)-6,6'-dimethylbiphenyl (referred to hereinafter as "T-biphemp"), 2,2'-bis(di(p-tert-Bu-phenyl)phosphino)-6,6'-dimethylbiphenyl (referred to hereinafter as "Bu-biphemp"), 2,2'-bis(di(p-methoxyphenyl)phosphino)-6,6'-dimethylbiphenyl (referred to hereinafter as "MeO-biphemp"), 2,2'-bis(di(p-chlorophenyl)phosphino)-6,6'-dimethylbiphenyl (referred to hereinafter as "Cl-biphemp"), 2,2'-bis(diphenylphosphino)-5,5',6,6',7,7',8,8'-octahydro-1,1'-binaphthyl (referred to hereinafter as "$H_8$binap"), 2,2'-bis(di(p-(p-tolyl)phosphino)-5,5',6,6',7,7',8,8'-octahydro-1,1'-binaphthyl (referred to hereinafter as "T-$H_8$binap"), 2,2'-bis(di(p-tert-Bu-phenyl)phosphino)-5,5',6,6',7,7',8,8'-octahydro-1,1'-binaphthyl (referred to hereinafter as "Bu-$H_8$binap"), 2,2'-bis(di(p-methoxyphenyl)phosphino)-5,5',6,6',7,7',8,8'-octahydro-1,1'-binaphthyl (referred to hereinafter as "MeO-H8binap"), 2,2'-bis(di(p-chlorophenyl)phosphino)-5,5',6,6',7,7',8,8'-octahydro-1,1'-binaphthyl (referred to hereinafter as "Cl-$H_8$binap"), 2,2'-bis(diphenylphosphino)-1,1'-binaphthyl (referred to hereinafter as "binap"), 2,2'-bis(di(p-tolyl)phosphino)-1,1'-binaphthyl (referred to hereinafter as "T-binap"), 2,2'-bis(di(p-tert-Bu-phenyl)phosphino)-1,1'-binaphthyl (referred to hereinafter as "Bu-binap"), 2,2'-bis(di(xylyl)phosphino)-1,1'-binaphthyl (referred to hereinafter as "Xy-binap"), 2,2'-bis(di(p-methoxyphenyl)phosphino)-1,1'-binaphthyl (referred to hereinafter as "MeO-binap"), 2,2'-bis(di(p-chlorophenyl)phosphino)-1,1'-binaphthyl (referred to hereinafter as "Cl-binap"), 2,2'-bis(di(cyclohexyl)phosphino)-1,1'-binaphthyl (referred to hereinafter as "Cy-binap"), 2,2'-bis(di(cyclopentyl)phosphino)-1,1'-binaphthyl (referred to hereinafter as "Cp-binap"), 2,2'-bis(diphenylphosphino)-5,5'-diamino-1,1-binaphthyl (referred to hereinafter as "NH-binap"), 2,2'-bis(diphenylphosphino)-5,5'-di(acetylamino)-1,1-binaphthyl (referred to hereinafter as "Ac-binap"), 2,2'-bis(diphenylphosphino)-5,5'-disulfo-1,1'-binaphthyl (referred to hereinafter as "$SO_2$-binap"), and disodium 2,2'-bis(diphenylphosphino)-1,1'-binaphthyl-5,5'-disulfonate (referred to hereinafter as "$SO_3Na$-binap").

The complex used in the present invention is formed from an optically active bidentate phosphine and a ruthenium compound, and specific examples include the following. A symbol for optical rotation, (+) or (−), is omitted for the following description of optically active bidentate phosphines.

The $Ru_xH_yCl_z(L)_2(S)_p$ type complex includes RuHCl(biphemp)$_2$, RuHCl(T-biphemp)$_2$, RuHCl(Bu-biphemp)$_2$, RuHCl(MeO-biphemp)$_2$, RuHCl(Cl-biphemp)$_2$, RuHCl($H_8$binap)$_2$, RuHCl(T-$H_8$binap)$_2$, RuHCl(Bu-$H_8$binap)$_2$, RuHCl(MeO-$H_8$binap)$_2$, RuHCl(Cl-$H_8$binap)$_2$, RuHCl(binap)$_2$, RuHCl(T-binap)$_2$, RuHCl(Bu-binap)$_2$, RuHCl(MeO-binap)$_2$, RuHCl(Cl-binap)$_2$, RuHCl(Xy-binap)$_2$, RuHCl(Cy-binap)$_2$, RuHCl(Cp-binap)$_2$, RuHCl(NH-binap)$_2$, RuHCl(Ac-binap)$_2$, RuHCl($SO_2$-binap)$_2$, RuHCl($SO_3Na$-binap)$_2$, etc., $Ru_2Cl_4$(biphemp)$_2$($NEt_3$), $Ru_2Cl_4$(T-biphemp)$_2$($NEt_3$), $Ru_2Cl_4$(Bu-biphemp)$_2$($NEt_3$), $Ru_2Cl_4$(MeO-biphemp)$_2$($NEt_3$), $Ru_2Cl_4$(Cl-biphemp)$_2$($NEt_3$), $Ru_2Cl_4$($H_8$binap)$_2$($NEt_3$), $Ru_2Cl_4$(T-$H_8$binap)$_2$($NEt_3$), $Ru_2Cl_4$(Bu-$H_8$binap)$_2$($NEt_3$), $Ru_2Cl_4$(MeO-$H_8$binap)$_2$($NEt_3$), $Ru_2Cl_4$(Cl-$H_8$binap)$_2$($NEt_3$), $Ru_2Cl_4$(binap)$_2$($NEt_3$), $Ru_2Cl_4$(T-binap)$_2$($NEt_3$), $Ru_2Cl_4$(Bu-binap)$_2$($NEt_3$), $Ru_2Cl_4$(MeO-binap)$_2$($NEt_3$), $Ru_2Cl_4$(Cl-binap)$_2$($NEt_3$), $Ru_2Cl_4$(Xy-binap)$_2$($NEt_3$), $Ru_2Cl_4$(Cy-binap)$_2$($NEt_3$), $Ru_2Cl_4$(Cp-binap)$_2$($NEt_3$), $Ru_2Cl_4$(NH-binap)$_2$($NEt_3$), $Ru_2Cl_4$(Ac-binap)$_2$($NEt_3$), $Ru_2Cl_4$($SO_2$-binap)$_2$($NEt_3$), $Ru_2Cl_4$($SO_3Na$-binap)$_2$($NEt_3$), etc.

The $Ru(OCOR^{14})_2(L)$ type complex includes Ru(OCOCH$_3$)$_2$(biphemp), Ru(OCOCH$_3$)$_2$(T-biphemp), Ru(OCOCH$_3$)$_2$(Bu-biphemp), Ru(OCOCH$_3$)$_2$(MeO-biphemp), Ru(OCOCH$_3$)$_2$(Cl-biphemp), Ru(OCOCH$_3$)$_2$($H_8$binap), Ru(OCOCH$_3$)$_2$(T-$H_8$binap), Ru(OCOCH$_3$)$_2$(Bu-$H_8$binap), Ru(OCOCH$_3$)$_2$(MeO-$H_8$binap), Ru(OCOCH$_3$)$_2$(Cl-$H_8$binap), Ru(OCOCH$_3$)$_2$(binap), Ru(OCOCH$_3$)$_2$(T-binap), Ru(OCOCH$_3$)$_2$(Bu-binap), Ru(OCOCH$_3$)$_2$(MeO-binap), Ru(OCOCH$_3$)$_2$(Cl-binap), Ru(OCOCH$_3$)$_2$(Xy-binap), Ru(OCOCH$_3$)$_2$(Cy-binap), Ru(OCOCH$_3$)$_2$(Cp-binap), Ru(OCOCH$_3$)$_2$(NH-binap), Ru(OCOCH$_3$)$_2$(Ac-binap), Ru(OCOCH$_3$)$_2$($SO_2$-binap), Ru(OCOCH$_3$)$_2$($SO_3Na$-binap), Ru(OCOCF$_3$)$_2$(biphemp), Ru(OCOCF$_3$)$_2$(T-biphemp), Ru(OCOCF$_3$)$_2$(Bu-biphemp), Ru(OCOCF$_3$)$_2$(MeO-biphemp), Ru(OCOCF$_3$)$_2$(Cl-biphemp), Ru(OCOCF$_3$)$_2$($H_8$binap), Ru(OCOCF$_3$)$_2$(T-$H_8$binap), Ru(OCOCF$_3$)$_2$(Bu-$H_8$binap), Ru(OCOCF$_3$)$_2$(MeO-$H_8$binap), Ru(OCOCF$_3$)$_2$(Cl-$H_8$binap), Ru(OCOCF$_3$)$_2$(binap), Ru(OCOCF$_3$)$_2$(T-binap), Ru(OCOCF$_3$)$_2$(Bu-binap), Ru(OCOCF$_3$)$_2$(MeO-binap), Ru(OCOCF$_3$)$_2$(Cl-binap), Ru(OCOCF$_3$)$_2$(Xy-binap), Ru(OCOCF$_3$)$_2$(Cy-binap), Ru(OCOCF$_3$)$_2$(Cp-binap), Ru(OCOCF$_3$)$_2$(NH-binap), Ru(OCOCF$_3$)$_2$(Ac-binap), Ru(OCOCF$_3$)$_2$($SO_2$-binap), Ru(OCOCF$_3$)$_2$($SO_3Na$-binap), Ru(OCOt-Bu)$_2$(biphemp), Ru(OCOt-Bu)$_2$(T-biphemp), Ru(OCOt-Bu)$_2$(Bu-biphemp), Ru(OCOt-Bu)$_2$(MeO-biphemp), Ru(OCOt-Bu)$_2$(Cl-biphemp), Ru(OCOt-Bu)$_2$($H_8$binap), Ru(OCOt-Bu)$_2$(T-$H_8$binap), Ru(OCOt-Bu)$_2$(Bu-$H_8$binap), Ru(OCOt-Bu)$_2$(MeO-$H_8$binap), Ru(OCOt-Bu)$_2$(Cl-$H_8$binap), Ru(OCOt-Bu)$_2$(binap), Ru(OCOt-Bu)$_2$(T-binap), Ru(OCOt- Bu)$_2$(Bu-binap), Ru(OCOt-Bu)$_2$(MeO-binap), Ru(OCOt-Bu)$_2$(Cl-binap), Ru(OCOt-Bu)$_2$ (Xy-binap), Ru(OCOt-Bu)$_2$(Cy-binap), Ru(OCOt-Bu)$_2$(Cp-binap), Ru(OCOt-Bu)$_2$ (NH-binap), Ru(OCOt-Bu)$_2$(Ac-binap), Ru(OCOt-Bu)$_2$ (SO$_2$-binap), Ru(OCOt-Bu)$_2$(SO$_3$Na-binap), etc.

The RuX$_2$(L) type complex includes RuCl$_2$(biphemp), RuCl$_2$(T-biphemp), RuCl$_2$(Bu-biphemp), RuCl$_2$(MeO-biphemp), RuCl$_2$(Cl-biphemp), RuCl$_2$(H$_8$binap), RuCl$_2$(T-H$_8$binap), RuCl$_2$(Bu-H$_8$binap), RuCl$_2$(MeO-H$_8$binap), RuCl$_2$(Cl-H$_8$binap), RuCl$_2$(binap), RuCl$_2$(T-binap), RuCl$_2$ (Bu-binap), RuCl$_2$(MeO-binap), RuCl$_2$(Cl-binap), RuCl$_2$ (Xy-binap), RuCl$_2$(Cy-binap), RuCl$_2$(Cp-binap), RuCl$_2$ (NH-binap), RuCl$_2$(Ac-binap), RuCl$_2$(SO$_2$-binap), RuCl$_2$ (SO3Na-binap), RuBr$_2$(biphemp), RuBr$_2$(T-biphemp), RuBr$_2$(Bu-biphemp), RuBr$_2$(MeO-biphemp), RuBr$_2$(Cl-biphemp), RuBr$_2$(H$_8$binap), RuBr$_2$(T-H$_8$binap), RuBr$_2$(Bu-H$_8$binap), RuBr$_2$(MeO-H$_8$binap), RuBr$_2$(Cl-H$_8$binap), RuBr$_2$(binap), RuBr$_2$(T-binap), RuBr$_2$(Bu-binap), RuBr$_2$ (MeO-binap), RuBr$_2$(Cl-binap), RuBr$_2$(Xy-binap), RuBr$_2$ (Cy-binap), RuBr$_2$(Cp-binap), RuBr$_2$(NH-binap), RuBr$_2$ (Ac-binap), RuBr$_2$(SO$_2$-binap), RuBr$_2$(SO$_3$Na-binap), etc.

The RuX$_k$J$_m$(L)Q$_n$ type complex includes [RuCl(benzene) (biphemp)]Cl, [RuI(p-cymene) (T-biphemp)]I, [RuBr(benzene) (Bu-biphemp)]Br, [RuCl(Bz-Me) (MeO-biphemp)]Cl (hereinafter, Bz-Me refers to methyl benzoate), [RuCl(benzene) (Cl-biphemp)]Cl, [RuI(benzene) (H$_8$binap)]I, [RuCl(benzene) (T-H$_8$binap)]Cl, [RuCl(p-cymene) (Bu-H$_8$binap)]Cl, [RuBr(benzene) (MeO-H$_8$binap)]Br, [RuCl(benzene) (Cl-H$_8$binap)]Cl, [RuI(p-cymene) (binap)]I, [RuI(p-cymene) (T-binap)]I, [RuCl (benzene) (T-binap)]Cl, [RuI(Me-Ar) (Bu-binap)]I, [RuBr (benzene) (MeO-binap)]Br, [RuCl(p-cymene) (Cl-binap)] Cl, [RuI(benzene) (T-binap)]I, [RuI(p-cymene) (Xy-binap)] I, [RuCl(benzene) (Cy-binap)]Cl, [RuI(Me-Ar) (Cp-binap)] I, [RuCl(benzene) (NH-binap)]Cl, [RuCl(benzene) (Ac-binap)]Cl, [RuBr (benzene) (SO$_2$-binap)]Br, [RuCl(p-cymene) (SO$_3$Na-binap)]Cl, [RuCl(benzene) (biphemp)] ClO$_4$, [RuCl(p-cymene) (T-biphemp)]ClO$_4$, [RuCl(benzene) (Bu-biphemp)]ClO$_4$, [RuCl(Me-Ar) (MeO-biphemp)]ClO$_4$, [RuCl(benzene) (Cl-biphemp)]ClO$_4$, [RuCl(benzene) (H$_8$binap)]ClO$_4$, [RuCl(benzene) (T-H$_8$binap)]ClO$_4$, [RuCl (p-cymene) (Bu-H$_8$binap)]ClO$_4$, [RuCl(benzene) (MeO-H$_8$binap)]ClO$_4$, [RuCl(benzene) (Cl-H$_8$binap)]ClO$_4$, [RuCl (p-cymene) (binap)]ClO$_4$, [RuCl(benzene) (T-binap)]ClO$_4$, [RuCl(Me-Ar) (Bu-binap)]ClO$_4$, [RuCl(benzene) (MeO-binap)]ClO$_4$, [RuCl(p-cymene) (Cl-binap)]ClO$_4$, [RuI (benzene) (Xy-binap)]ClO$_4$, [RuCl(p-cymene) (Xy-binap)] ClO$_4$, [RuI(benzene) (Cy-binap)]ClO$_4$, [RuCl(p-cymene) (Cy-binap)]ClO$_4$, [RuCl(Me-Ar) (Cp-binap)]ClO$_4$, [RuCl (benzene) (NH-binap)]ClO$_4$, [RuCl(benzene) (Ac-binap)] ClO$_4$, [RuCl(benzene) (SO$_2$-binap) ClO$_4$, [RuCl(p-cymene) (SO$_3$Na-binap)]ClO$_4$, etc., [RuCl(CH$_3$CN)$_2$(biphemp)]Cl, [RuCl(CH$_3$CN)$_2$(T-biphemp)]Cl, [RuCl(CH$_3$CN)$_2$(Bu-biphemp)]Cl, [RuCl(CH$_3$CN)$_2$(MeO-biphemp)]Cl, [RuCl (CH$_3$CN)$_2$(Cl-biphemp)]Cl, [RuCl(CH$_3$CN)$_2$(H$_8$binap)]Cl, [RuCl(CH$_3$CN)$_2$(binap)]Cl, [RuCl(CH$_3$CN)$_2$(T-binap)]Cl, [RuCl(CH$_3$CN)$_2$(Cy-binap)]Cl, [Ru(CH$_3$CN)$_4$(binap)] (ClO$_4$)$_2$, [Ru(CH$_3$CN)$_4$(T-binap)](BF$_4$)$_2$, [Ru(CH$_3$CN)$_4$ (binap)](PF$_6$)$_2$, etc.

These complexes can be produced, for example, using the following methods:

(i) Ru$_x$H$_y$Cl$_z$(L)$_2$(S)$_p$ type complex

Synthesis of the Ru$_x$H$_y$Cl$_z$(L)$_2$(S)$_p$ type complex can be carried out according to the method described by T. Ikariya et al., *Journal Chemical Society Chemical Communication,* 922, 1985 or Japanese Patent Application Laid-Open No. 61-63690. For example, for the complex where y=0, one molar equivalent of [RuCl$_2$(COD)]$_n$ (n is an integer) obtained by reacting ruthenium chloride with 1,5-cyclooctadiene (COD) in an alcohol solvent such as ethanol, etc., is reacted with 1.05 to 1.2 molar equivalents of bidentate phosphine in the presence of 4 molar equivalents of a tertiary amine in a solvent such as toluene, ethanol or the like to obtain the object compound. The complex where y=1 can be obtained by the same method as described above where bidentate phosphine L is used in a 2-fold molar excess amount relative to [RuCl$_2$(COD)]$_n$.

(ii) Ru(OCOR$^{14}$)$_2$(L) type complex

The Ru(OCOR$^{14}$)$_2$(L) type complex can be obtained according to the method described in Japanese Patent Application Laid-Open No. 61-63690. For example, Ru$_2$Cl$_4$(L)$_2$ (NEt$_3$) obtained in (i) above is reacted as a starting material with a lower carboxylate represented by R$^{14}$COOM (R$^{14}$ and M have the same meanings as defined above) in an alcohol solvent such as methanol, ethanol, tert-butanol, etc., at a temperature of about 20 to 110° C. for 3 to 15 hours. Then, the solvent is removed by distillation. The object complex is extracted with a solvent such as ether, ethanol, etc., and then dried to obtain the complex in a crude form. A purified preparation can be obtained by further recrystallizing the crude product from ethyl acetate, etc.

(iii) RuX$_2$(L) type complex

The RuX$_2$(L) type complex can be obtained according to the method described in Japanese Patent Application Laid-open No. 63-145292. For example, Ru$_2$Cl$_4$(L)$_2$(NEt$_3$) obtained in (i) above is reacted with a salt represented by MQ (M and Q have the same meanings as defined above) in a mixed solvent of water and methylene chloride, using as a phase-transfer catalyst a quaternary ammonium salt or quaternary phosphonium salt represented by the following general formula (15):

$$R^{16}R^{17}R^{18}R^{19}ZX \qquad (15)$$

wherein R$^{16}$, R$^{17}$, R$^{18}$ and R$^{19}$ each represents a C1 to C16 alkyl group, a phenyl group or a benzyl group, Z represents a nitrogen atom or a phosphorus atom, and X has the same meaning as defined above).

The salt used herein includes perchlorates with sodium, potassium, lithium, etc., tetrafluoroborate and hexafluorophosphite, and the phase-transfer catalyst used herein includes quaternary ammonium salts such as tetramethyl ammonium bromide, tetrapropyl ammonium bromide, tetrabutyl ammonium chloride, tetrabutyl ammonium iodide, octyl trimethyl ammonium bromide, lauryl trimethyl ammonium bromide, lauryl triphenyl ammonium bromide, cetyl trimethyl ammonium bromide, methyl trioctyl ammonium chloride and benzyl triethyl ammonium bromide, as well as their corresponding quaternary phosphonium salts.

(iv) RuX$_k$J$_m$(L)Q$_n$ type complex

The RuX$_k$J$_m$(L)Q$_n$ type complex can be obtained according to the method described in Japanese Patent Application Laid-Open No. 2-192189. For example, the complex where J is benzene, p-cymene or lower alkyl benzoate can be obtained in the following manner. The above complex in which both X and Q are chlorine atoms can be obtained by reacting [RuCl$_2$J]$_2$ as a starting material with bidentate phosphine L at 25 to 50° C. for 30 minutes to 3 hours in a single solvent such as methanol, ethanol, benzene, methylene chloride, etc., or in a mixed solvent thereof, and then removing the solvent by distilling under reduced pressure. When both X and Q are bromine atoms or iodine atoms, [RuCl$_2$J]$_2$ is reacted as a starting material with a salt represented by MBr or MI (M has the same meaning as defined above), using water as solvent or using a phase-transfer catalyst represented by general formula (14) in a mixed solvent of water and methylene chloride, to thereby obtain [RuBr$_2$J]$_2$ or [RuI$_2$J]$_2$. Then, the resulting [RuBr$_2$J]$_2$ or [RuI$_2$J]$_2$ is reacted at 25 to 50° C. for 30 minutes to 3 hours with bidentate phosphine L in a single solvent such as methanol, ethanol, benzene, methylene chloride, etc., or in a mixed solvent thereof, and the solvent is then removed by distilling under reduced pressure to obtain the object complex. When Q is other than a halogen atom, a complex such as [RuCl(J) (L)]Cl obtained above is dissolved in methanol, ethanol, benzene, methylene chloride, etc., and a salt represented by MQ' (M has the same meaning as defined above, and Q' represents ClO$_4$, BF$_4$ and PF$_6$) is added thereto. Then, the mixture is stirred, a small amount of insolubles are filtered off, and the filtrate is concentrated and dried to obtain the object complex. When J is acetonitrile, a complex such as [RuCl(J) (L)]Cl is dissolved in acetonitrile and refluxed at 50° C. for 10 to 24 hours, and excess acetonitrile is removed by distillation, and the resulting product is dried. This crude complex is recrystallized from methylene chloride to obtain [RuCl(CH$_3$CN) (L)]Cl. For example, [RuCl(J) (L)]Cl complex is dissolved in a mixed solvent of acetonitrile and methanol, ethanol, benzene, methylene chloride or the like, and MQ' (M has the same meaning as defined above) is added thereto. Then, the mixture is stirred at 25 to 50° C. for 10 to 24 hours, the solvent is removed by distillation, and the product is dried and then recrystallized from methylene chloride, to thereby obtain a complex such as [Ru(CH$_3$CN)$_4$(L)](ClO$_4$)$_2$.

To carry out the asymmetric hydrogenation of the present invention, 3-acetyl-1-benzyl-2-pyrrolidinone (Compound (1)) is dissolved in a single solvent selected from alcohols such as methanol, ethanol, isopropanol, etc., ketones such as acetone, methyl ethyl ketone, methyl isobutyl ketone, cyclohexanone, etc., ethers such as tetrahydrofuran, 1,3-dioxolane, diethyl ether, di-isopropyl ether, etc., esters such as ethyl acetate, butyl acetate, etc., aromatic hydrocarbons such as benzene, toluene, xylene, etc., halogenated hydrocarbons such as methylene chloride, etc., or a mixture thereof and subjected to asymmetric hydrogenation in an autoclave. In this reaction, a ruthenium/bidentate phosphine complex is added in an amount of 1/10000 to 1/10 mole, preferably 1/2000 to 1/100 mole, per mole of Compound (1) as the substrate, and hydrogenation is carried out at with stirring at a hydrogen pressure of 5 to 100 kg/cm$^2$, preferably 30 to 60 kg/cm$^2$, and a reaction temperature of 25 to 100° C., preferably 40 to 70° C. The time required for this reaction is 3 to 100 hours, preferably 8 to 24 hours, depending on the reaction temperature. The resulting optically active 1-benzyl-3-[(1'-hydroxy)ethyl]-2-pyrrolidinone can be purified to a high degree in terms of optical purity and diastereomeric purity by recrystallizing from an organic solvent such as toluene, ethyl acetate, acetone or the like.

Then, (3S,1'R)-1-benzyl-3-[(1'-hydroxy)ethyl]-2-pyrrolidinone (Compound (2)) obtained in the manner described above is reduced with a known amide group-reducing reagent to convert the same into the corresponding amine, i.e., (3R,1'R)-1-benzyl-3-[(1'-hydroxy)ethyl]-2-pyrrolidine. Specifically, it is reduced with a reducing agent such as lithium aluminum hydride, borane, etc., or by a combination of sodium borohydride and a Lewis acid, as described by M. Hudliky in *Reduction in Organic Chemistry* (John Wiley & Sons Ltd.). Furthermore, reduction of a side-chain amide by sodium borohydride and sulfuric acid can be carried out as described in Japanese Patent Application Laid-Open No. 8-169877, but in the present invention, it was found that pyrrolidinone, i.e., a cyclic amide group, can be reduced into pyrrolidine. The solvent used for this reaction includes ethers such as diethyl ether, di-isopropyl ether, dimethoxyethane, tetrahydrofuran, etc., among which tetrahydrofuran is preferred. In the case of lithium aluminum hydride, the amount of the reducing agent is 1 to 4 molar equivalents, preferably 2 molar equivalents, relative to Compound (2) as the substrate. The reaction temperature ranges from 0 to 70° C. depending on the solvent used. If sodium borohydride and sulfuric acid are used in the present invention, sodium borohydride is used in an amount of 2 to 4 molar equivalents, preferably 3 molar equivalents, and sulfuric acid is used in an amount of 1 to 2 molar equivalents, preferably 1.5 molar equivalents, relative to Compound (2) as the substrate. The reaction temperature ranges from 0 to 50° C. depending on the solvent used. If sodium borohydride and sulfuric acid are used, 1 molecule of borane is bound to the reduced product (amine compound) to form a borane complex, and this product is heat-treated with a mineral acid such as hydrochloric acid or sulfuric acid to provide a free amine compound (3R,1'R)-1-benzyl-3-[(1'-hydroxy)ethyl]-2-pyrrolidine. Although this product can be used in the subsequent step without purification, a highly purified preparation can be obtained by vacuum distillation.

Then, (3R,1'R)-1-benzyl-3-[(1'-hydroxy)ethyl] pyrrolidine (Compound (3)) obtained in the manner described above is reacted with methanesulfonyl chloride or paratoluene sulfonyl chloride, preferably in the presence of a tertiary amine, to obtain Compound (4), i.e., (3R,1'R)-1-benzyl-3-[(1'-methanesulfonyloxy)ethyl]pyrrolidine or (3R,1'R)-1-benzyl-3-[(1'-p-toluenesulfonyloxy)ethyl]pyrrolidine. The tertiary amine for use in the present invention includes triethyl amine, tributyl amine, ethyl di-isopropyl amine, dimethyl aniline, pyridine, N-methylpiperidine, etc., among which triethyl amine is particularly preferred. The amount of the tertiary amine is at least an equivalent molar amount relative to Compound (3) as the substrate. The reaction temperature is in the range of 0 to 35° C., preferably 10 to 20° C.

The resulting product (3R,1'R)-1-benzyl-3-[(1'-methanesulfonyloxy)ethyl] pyrrolidine or (3R,1'R)-1-benzyl-3-[(1'-paratoluenesulfonyloxy)ethyl]pyrrolidine can be used in the subsequent step without purification. That is, (3R,1'R)-1-benzyl-3-[(1'-methanesulfonyloxy)ethyl] pyrrolidine (4a) or (3R,1'R)-1-benzyl-3-[(1'-paratoluenesulfonyloxy)ethyl]-pyrrolidine (4b), or both of these compounds, are reacted under heating with methylamine in an organic solvent to obtain (3R,1'S)-1-benzyl-3-[(1'-N-methylamino)ethyl]pyrrolidine as Compound (5). The solvent for use in this reaction includes aliphatic hydrocarbons such as hexane, heptane, cyclohexane, etc., aromatic hydrocarbons such as benzene, toluene, xylene, etc., alcohols such as methanol, ethanol, isopropanol, tert-butanol, etc., amides such as dimethylformamide, dimethylacetamide, etc., nitrites such as acetonitrile, etc., and ethers such as diethyl ether, di-isopropyl ether, dimethoxy ethane, tetrahydrofuran, etc. These solvents can be used singly or in combination. Tetrahydrofuran is preferably used. The reaction temperature is in the range of 10 to 120° C., preferably 60 to 90° C. The reaction time is in the range of 4 to 48 hours, preferably 8 to 40 hours. The amount of methylamine is 10 to 50% by weight, preferably 30% by weight, relative to the solvent. In this methylamination, inversion at the 1'-position occurs in its conformation. Although olefin compounds from which a mesyl group or tosyl group has been eliminated occur as by-products, (3R,1'S)-1-benzyl-3-[(1'-N-methylamino) ethyl] pyrrolidine (5) of high purity can be obtained by vacuum distillation.

(3R,1'S)-1-benzyl-3-[(1'-N-methylamino)ethyl] pyrrolidine (5) is further subjected de-benzylation by a known method for removing a protective group, as described in *Protective Group in Organic Synthesis* (published by John Wiley & Sons, 1981), for example, by hydrogenating with palladium carbon, etc. as a catalyst to obtain (3R,1'S)-3-[(1'-N-methylamino)ethyl]-pyrrolidine (14).

According to the present invention, (3R,1'S)-1-benzyl-3-[(1'-N-methylamino)ethyl]pyrrolidine or (3R,1'S)-3-[(1'-N-methylamino)ethyl]pyrrolidine that is an intermediate for the synthesis of quinolone type anti-fungus agents can be obtained in higher purity and in higher yield by a safe process and with fewer steps than in conventional processes.

EXAMPLES

Hereinafter, the present invention is described in greater detail by reference to the following Examples, which however are not intended to limit the present invention. The physical data in the Examples were obtained using the following measurement instruments and conditions:

(A) Chemical purity, optical purity and diastereomeric selectivity: Gas chromatography HP-5890 (Hewlett Packard Ltd.)

Column: Silicon NB-1 (0.25 mm×30 m) produced by G. L. Science

Temperature: a gradient of from 100 to 220° C. at a rate of 10° C. /min.

Liquid chromatography L-6000 pump, L-4000 UV (Hitachi, Ltd.)

Column-1: Inertosil ODS-2 (4.6 mm×250 mm)

Solvent: acetonitrile/water=7/3, pH 2.3 (phosphate)

Flow rate: 0.5 ml/min.

Detection: 254 nm

Column-2: CHIRALPAK AD (4.6 mm×250 mm)

Solvent: hexane/isopropanol/ethanol=90/5/5

Flow rate: 0.5 ml/min.

Detection: 220 nm (B) Proton nuclear magnetic resonance spectrum ($^1$H-NMR): AM-400 (Bruker Co., Ltd.), internal standard; tetramethyl silane (C) Specific rotation: DIP-4 (Nihon Bunkoh Co., Ltd)

(D) Melting point: MP-S3 (Yanagimoto Shoji K.K.)

Example 1

Synthesis of (3S,1'R)-1-benzyl-3-[(1'-hydroxy) ethyl]-2-pyrrolidinone (2)

A 1000-ml autoclave was charged with 113.1 g (521 mM) 3-acetyl-1-benzyl-2-pyrrolidinone (1), 340 ml methylene chloride and 0.76 g (0.65 mM) [RuI(p-cymene) {(+)-T-binap}] I, and the mixture was reacted at a hydrogen pressure of 50 kg/cm$^2$ at 50 to 55° C. for 21 hours. The optical yield and diastereomeric selectivity as determined by HPLC column-2 were 87.9%ee and 98.8%de, respectively. The solvent was recovered under reduced pressure, and the residue was dissolved with 340 ml toluene, stirred, dissolved and crystallized at 0° C. The precipitated crystal was filtered to provide 95.6 g of the title compound (2) as a white crystal (yield, 83.7%; chemical purity as determined by gas chromatography, 99%; optical purity as determined by HPLC column-2, 99%ee; diastereomeric selectivity as determined by HPLC column-2, 99%de; and melting point, 82 to 82.5° C.).

Specific rotation $[\alpha]_D^{23}$=−10.43° (c=1.15, CHCl$_3$)

$^1$H-NMR (CDCl$_3$, δppm) 1.18 (3H, d, J=6.6 Hz), 1.91–2.04 (2H, m), 2.52–2.62 (1H, m), 3.36 (1H, d, J=5.6 Hz), 3.12–3.20 (2H, m), 4.21–4.38 (1H, m), 4.42 (2H, s), 7.16–7.29 (5H, m).

Examples 2 to 9

Synthesis was carried out in the same manner as in Example 1, except that isopropanol, acetone, tetrahydrofuran, methyl ethyl ketone, methyl isobutyl ketone, cyclohexanone, ethyl acetate and butyl acetate were used respectively as the solvent in place of methylene chloride. The results are shown in Table 1.

TABLE 1

|  | Solvent | Diastereomeric Selectivity | Optical Purity |
| --- | --- | --- | --- |
| Example 2 | isopropanol | 95.5% de | 47.5% ee |
| Example 3 | acetone | 97.1% de | 74.0% ee |
| Example 4 | tetrahydroturan | 96.1% de | 81.5% ee |
| Example 5 | methyl ethyl ketone | 95.7% de | 82.4% ee |
| Example 6 | methyl isobutyl ketone | 93.6% de | 81.5% ee |
| Example 7 | cyclohexanone | 93.9% de | 80.7% ee |
| Example 8 | ethyl acetate | 94.2% de | 83.8% ee |
| Example 9 | butyl acetate | 95.5% de | 81.0% ee |

Examples 10 to 13

Synthesis was carried out in the same manner as in Example 1, except that [RuI(p-cymene) {(+)-binap}]I, Ru$_2$Cl$_4$[(+)-binap]$_2$NEt$_3$, Ru(OCOCH$_3$)$_2$[(+)-binap] and [RuI(p-cymene)]{(+)-Xy-binap}I were used respectively as the asymmetric hydrogenation catalyst in place of [RuI(p-cymene) {(+)-T-binap}]I, and the reaction time was varied. The results are shown in Table 2.

TABLE 2

|  | Catalyst | Reaction Time | Diastereomeric | Optical Selectivity |
| --- | --- | --- | --- | --- |
| Example 10 | [RuI(p-cymene) {(+)-binap}] I | 17 h | 99.2% de | 89.3% ee |
| Example 11 | Ru$_2$Cl$_4$[(+)-binap]$_2$NEt$_3$ | 89 h | 99.0% de | 82.5% ee |
| Example 12 | Ru(OCOCH$_3$)$_2$[(+)-binap] | 51 h | 52.5% de | 54.3% ee |
| Example 13 | [RuI(p-cymene)] {(+)-Xy-binap}]I | 41 h | 93.0% de | 86.1% ee |

Similarly, when Ru$_2$Cl$_4$[(+)-T-binap]$_2$NEt$_3$ was used as the asymmetric hydrogenation catalyst, the reaction time was 80 hours, the diastereomeric selectivity was 98.0%de and the optical purity was 80.0%ee. When Ru$_2$Cl$_4$[(+)-biphemp]$_2$NEt$_3$ was used, the reaction time was 65 hours, the diastereomeric selectivity was 95.5%de and the optical purity was 78.5%ee. When [RuI(p-cymene){(+)-H$_8$binap}]I was used, the reaction time was 35 hours, the diastereomeric selectivity was 93.5%de and the optical purity was 82.0%ee.

Example 14

Synthesis of (3R,1'R)-1-benzyl-3-[(1'-hydroxy) ethyl]pyrrolidine (3)

85.9 g (0.393 M) of (3S,1'R)-1-benzyl-3-[(1'-hydroxy) ethyl]-2-pyrrolidinone (2) obtained in Example 1 was dissolved in 430 ml tetrahydrofuran and cooled at 10 to 15° C., and 44.5 g (1.2 M) of sodium borohydride was added thereto all at once. Furthermore, 57.7 g (0.589 M) of conc. sulfuric acid was added dropwise thereto over a period of 65 minutes. Thereafter, the reaction solution was heated at 40 to 60° C. for 4 hours. The reaction solution was then cooled and the tetrahydrofuran was removed under reduced pressure. Then, 200 ml of ice-cold water was carefully added, and 400 ml of 6 N hydrochloric acid and 200 ml water were added, and the mixture was stirred under heating at 50° C. for 2 hours. After cooling, the solution was adjusted to pH 10–12 with sodium hydroxide, and then extracted with 900 ml of ethyl acetate. The extract was washed with 500 ml water and then dried over magnesium sulfate anhydride, and the solvent was recovered under reduced pressure, to thereby obtain 72.0 g of the title compound (3) as an oily residue (chemical purity as determined by HPLC column-1, 99%; yield, 89%; boiling point, 107 to 110° C./0.3 mmHg).

Specific rotation $[\alpha]_D^{23}$=+9.00° (c=1.1, CHCl$_3$)

$^1$H-NMR (CDCl$_3$, δppm) 1.08 (3H, d, J=6.3 Hz), 1.79–1.91 (2H, m), 2.08–2.11 (1H, m), 2.21–2.28 (1H, m), 2.42–2.46 (1H, m), 2.66–2.69 (1H, m), 3.58 (1H, s), 3.83–3.89 (1H, m), 7.24–7.32 (5H, m).

Example 15

Synthesis of (3R,1'R)-1-benzyl-3-[(1'-hydroxy)ethyl] pyrrolidine (3)

10 g (45.6 mM) of (3S,1'R)-1-benzyl-3-[(1'-hydroxy)ethyl]-2-pyrrolidinone (2) obtained in Example 1 was dissolved in 20 ml tetrahydrofuran, then cooled at 10 to 15° C. and added dropwise to a suspension of 3.47 g (91 mM) of lithium aluminum hydride in 50 ml tetrahydrofuran over a period of 30 minutes. Thereafter, the mixture was refluxed under heating at 70° C. for 2 hours. The reaction solution was cooled and the tetrahydrofuran was removed under reduced pressure. Then, a 10% aqueous sodium hydroxide solution and 60 ml of water were carefully added thereto. The product was extracted with 200 ml of ethyl acetate, then washed with water and dried over magnesium sulfate anhydride. The solvent was then recovered under reduced pressure, to thereby obtain 8.9 g of the title compound (3) as an oily residue (yield, 95%).

Example 16

Synthesis of (3R,1'R)-1-benzyl-3-[(1'-methanesulfonyloxy)ethyl] pyrrolidine (4a)

75.0 g (0.366 M) of (3R,1'R)-1-benzyl-3-[(1'-hydroxy)ethyl]pyrrolidine (3) obtained in Example 15 was dissolved in 360 ml toluene, 61.1 ml (44.4 g, 0.439 M) of triethyl amine was added thereto, and the mixture was cooled at 10° C. or less. A mixture of 33.9 ml (50.2 g, 0.439 M) methanesulfonyl chloride and 35 ml toluene was added thereto over a period of 40 minutes. The reaction solution was stirred as such for 1 hour, 400 ml of water was added thereto, and the organic layer was extracted. The aqueous layer was adjusted to pH 9 with sodium hydroxide, further extracted with 300 ml toluene and combined with the organic layer, and the combined extract was washed with 10% brine. The product was dried over magnesium sulfate anhydride, and the solvent was recovered under reduced pressure to obtain 98.4 g of the title compound (4a) as an oily residue (chemical purity as determined by HPLC column-1, 94.8%; yield, 95%).

$^1$H-NMR (CDCl$_3$, δppm) 1.39 (3H, d, J=6.3 Hz), 1.70–1.77 (1H, m), 2.00–2.03 (1H, m), 2.27–2.31 (1H, m), 2.45–2.47 (1H, m), 2.51–2.57 (1H, m), 2.70–2.80 (2H, m), 2.98 (3H, s), 3.62 (1H, d, J=12.9 Hz), 3.67 (1H, d, J=12.9 Hz), 4.69–4.76 (1H, m), 7.24–7.34 (5H, m).

Example 17

Synthesis of (3R,1'R)-1-benzyl-3-[(1'-paratoluenesulfonyloxy)ethyl]-pyrrolidine (4b)

4.1 g (20 mM) of (3R,1'R)-1-benzyl-3-[(1'-hydroxy)ethyl]pyrrolidine (3) obtained in Example 15 was dissolved in 25 ml toluene, 2.78 ml (2.02 g, 20 M) of triethyl amine was added thereto, and the mixture was cooled to 10° C. or less. 3.81 g (20 mM) of p-toluenesulfonyl chloride was then added to the reaction mixture. The reaction mixture was stirred as such for 18 hours, and then 80 ml water was added thereto. The organic layer was then extracted and washed with 10% brine. The product was dried over magnesium sulfate anhydride, and the solvent was recovered under reduced pressure, to obtain 6.45 g of the title compound (4b) as an oily residue (yield: 90%).

$^1$H-NMR (CDCl$_3$, δppm) 1.13 (3H, d, J=6.3 Hz), 1.62–1.72 (2H, m), 1.91–2.00 (1H, m), 2.01–2.11 (1H, m), 2.44 (3H, s), 2.90–2.95 (1H, m), 3.14–3.20 (2H, m), 3.27–3.32 (2H, m), 3.55–3.62 (1H, m), 7.28–7.35 (5H, m), 7.70 (2H, d, J=1.8 Hz), 7.72 (2H, d, J=1.8 Hz).

Example 18

Synthesis of (3R,1'S)-1-benzyl-3-[(1'-N-methylamino)ethyl] pyrrolidine (5)

A previously cooled pressure-resistant vessel having a capacity of 500 ml was charged with 33.5 g of methylamine, followed by adding 90 ml of a tetrahydrofuran solution (methylamine concentration: 30 wt %) containing 50.9 g (0.18 M) of the (3R,1'R)-1-benzyl-3-[(1'-methanesulfonyloxy)ethyl]pyrrolidine (4a) obtained in Example 16, and the mixture was stirred under heating at 80° C. for 15 hours. The selectivity of (3R,1'S)-1-benzyl-3-[(1'-N-methylamino)ethyl]pyrrolidine (5) as determined by gas chromatography was 77.1%. After cooling, the solvent was recovered under reduced pressure, and 250 ml of toluene and 250 ml of water were added to the remaining crystal and oily residue. The toluene layer thus separated was concentrated under reduced pressure to provide 38.2 g of an oily residue. This residue was subjected to vacuum distillation to obtain 31.8 g of the title compound (5) (boiling point, 115 to 120° C./1.5 mmHg; chemical purity as determined by gas chromatography, 85.9%; yield, 58.5%).

$^1$H-NMR (CDCl$_3$, δppm) 1.02 (3H, d, J=6.2 Hz), 1.46–1.54 (1H, m), 1.87–1.95 (1H, m), 2.09–2.19 (1H, m), 2.25–2.27 (1H, m), 2.37 (3H, s), 2.37–2.46 (2H, m), 2.62–2.66 (1H, m), 2.74–2.79 (1H, m), 3.57 (1H, d, J=12.9 Hz), 3.61 (1H, d, J=12.9 Hz), 7.21–7.33 (5H, m).

Example 19

Synthesis of (3R,1'S)-1-benzyl-3-[(1'-N-methylamino)ethyl] pyrrolidine (5)

A pressure-resistant vessel having a capacity of 100 ml was charged with 12 ml of a methanol solution containing 40 wt % methylamine, followed by adding 10 ml of a tetrahydrofuran solution containing 4.0 g (11 mM) of the (3R,1'R)-1-benzyl-3-[(1'-paratoluenesulfonyloxy)ethyl]pyrrolidine (4b) obtained in Example 17, and the mixture was stirred under heating at 80° C. for 18 hours. After cooling, the solvent was recovered under reduced pressure, and 50 ml of toluene and 50 ml of water were added to the remaining oily residue. The toluene layer thus separated was concentrated under reduced pressure to provide 2.9 g of an oily residue. This residue was vacuum distilled to obtain 1.2 g of the title compound (5) (boiling point, 100 to 120° C./1.5 mmHg; chemical purity as determined by gas chromatography, 69.1%; yield, 34.5%).

Examples 20 to 31

Synthesis was carried out in the same manner as in Example 18, except that toluene, xylene, methanol, acetonitrile, 1,3-dioxolane, di-isopropyl ether, dimethoxyethane, dibutyl ether, tertiary butyl methyl ether, dimethylformamide, monomethylformamide and monomethylacetamide were used respectively as the solvent in place of tetrahydrofuran, and methylamine having a concentration of 20% by weight was used. The results are shown in Table 3.

TABLE 3

|  | Solvent | Selectivity of Compound (5) |
|---|---|---|
| Example 20 | toluene | 58.5% |
| Example 21 | xylene | 49.0% |
| Example 22 | methanol | 45.5% |
| Example 23 | acetonitrile | 16.7% |
| Example 24 | 1,3-dioxolane | 31.4% |
| Example 25 | di-isopropyl ether | 19.0% |
| Example 26 | dimethoxyethane | 66.5% |
| Example 27 | dibutyl ether | 35.0% |
| Example 28 | t-butylmethyl ether | 54.8% |
| Example 29 | dimethylformamide | 40.4% |
| Example 30 | monomethylformamide | 23.8% |
| Example 31 | monomethylacetamide | 40.9% |

Example 32 to 35

Synthesis was carried out in the same manner as in Examples 18, except that the concentration of methylamine was varied. The results are shown in Table 4.

TABLE 4

|  | Concentration of Methylamine | Selectivity of Compound (5) |
|---|---|---|
| Example 32 | 10 wt % | 60.7% |
| Example 33 | 20 wt % | 72.2% |
| Example 34 | 40 wt % | 68.2% |
| Example 35 | 50 wt % | 64.9% |

Reference Example 1

Synthesis of (3R,1'S)-3-[(1'-N-methylamino)ethyl] pyrrolidine (14)

A 1000-ml autoclave was charged with 4.5 g of 5% palladium on carbon and a solution prepared by dissolving, in 225 ml of methanol, 45.0 g (0.206 M; chemical purity, 85.9%) of (3R,1'S)-1-benzyl-3-[(1'-N-methylamino)ethyl] pyrrolidine (5) obtained in Example 18. The mixture was stirred under heating at 65° C. for 18 hours at a hydrogen pressure of 30 atm. The catalyst was removed by filtration and the solvent was recovered under reduced pressure, and the remaining oily residue, 37.9 g, was vacuum distilled to obtain 20.3 g of the title compound (14) (yield, 85%; boiling point, 80 to 82° C./11 mmHg; chemical purity as determined by gas chromatography, 95.3%).

Specific rotation $[\alpha]_D^{24}$=+37.25° (c=1.16, EtOH)

$^1$H-NMR (CDCl$_3$, δppm) 1.06 (3H, d, J=6.2 Hz), 1.36–1.45 (1H, m), 1.72 (1H, br. s), 1.81–1.89 (1H, m), 1.95–2.06 (1H, m), 2.40 (3H, s), 2.38–2.45 (2H, m), 2.59–2.64 (1H, m), 2.86–2.97 (2H, m), 3.08–3.13 (1H, m).

While the invention has been described in detail and with reference to specific embodiments thereof, it will be apparent to one skilled in the art that various changes and modifications can be made therein without departing from the spirit and scope thereof.

What is claimed is:

1. A process for producing (3R,1'S)-1-benzyl-3-[(1'-N-methylamino)ethyl]pyrrolidine represented by formula (5):

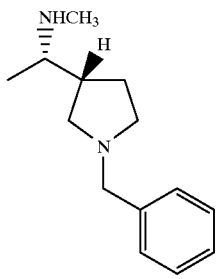

(5)

which comprises asymmetrically hydrogenating 3-acetyl-1-benzyl-2-pyrrolidinone represented by formula (1):

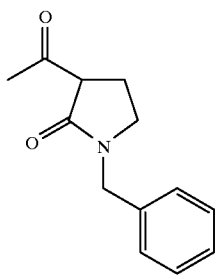

(1)

in the presence of a complex formed from bidentate phosphine and ruthenium as a catalyst to produce (3S,1'R)-1-benzyl-3-[(1'-hydroxy)ethyl]-2-pyrrolidinone represented by formula (2):

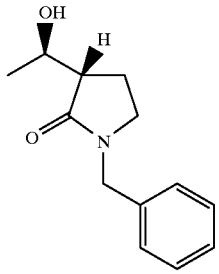

(2)

reducing the resulting (3S,1'R)-1-benzyl-3-[(1'-hydroxy) ethyl]-2-pyrrolidinone to produce (3R,1'R)-1-benzyl-3-[(1'-hydroxy)ethyl]pyrrolidine represented by formula (3):

(3)

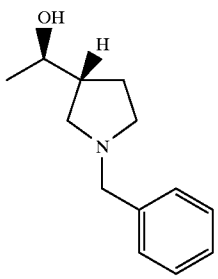

mesylating and/or tosylating the resulting (3R,1'R)-1-benzyl-3-[(1'-hydroxy)ethyl]pyrrolidine to produce (3R,1'R)-1-benzyl-3-[(1'-methanesulfonyloxy)ethyl]pyrrolidine and/or (3R,1'R)-1-benzyl-3-[(1'-paratoluenesulfonyloxy)ethyl]pyrrolidine represented by formula (4):

(4)

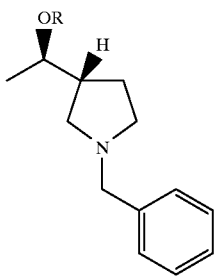

wherein R represents a methanesulfonyl group or a p-toluenesulfonyl group, and methylaminating the resulting (3R,1'R)-1-benzyl-3-[(1'-methanesulfonyloxy)ethyl] pyrrolidine or (3R,1'R)-1-benzyl-3-[(1'-p-toluenesulfonyloxy)ethyl]pyrrolidine, wherein the bidentate phosphine comprises a bidentate phosphine L represented by the following general formula (6):

(6)

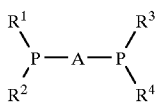

wherein $R^1$, $R^2$, $R^3$ and $R^4$ may be the same or different and each represents a phenyl group, a cyclohexyl group, a cyclopentyl group, a $C_1$ to $C_4$ lower alkyl group, a $C_1$ to $C_4$ lower alkoxy group or a halogen-substituted phenyl group; A is represented by the following general formula (7):

(7)

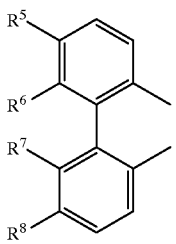

wherein $R^5$ and $R^8$ each represents a hydrogen atom and $R^6$ and $R^7$ each represents a methyl group, or $R^5$ and R6 or $R^7$ and $R^8$ may combine to form a tetramethylene group, or A is represented by the following general formula (8):

(8)

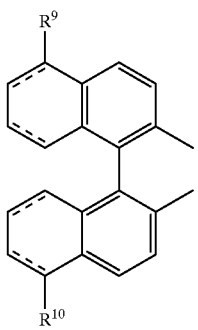

wherein $R^9$ and $R^{10}$ may be the same or different and each represents a hydrogen atom, an amino group, an acetylamino group or —$SO_3M$ where M represents a hydrogen atom or an alkali metal atom and the broken line is a saturated or double bond.

2. The process for producing (3R,1'S)-1-benzyl-3-[(1'-N-methylamino)ethyl] pyrrolidine according to claim 1, wherein the complex formed from bidentate phosphine and ruthenium comprises a complex represented by the following general formula (9):

$$Ru_xH_yCl_z(L)_2(S)_p \qquad (9)$$

wherein L is as defined in claim 1 and S is represented by the following general formula (10):

$$NR^{11}R^{12}R^{13} \qquad (10)$$

wherein $R^{11}$, $R^{12}$ and $R^{13}$ may be the same or different and each represents a lower alkyl group; wherein y is 0, x is 2, z is 4 and p is 1; or wherein y is 1, x is 1, z is 1 and p is 0.

3. The process for producing (3R,1'S)-1-benzyl-3-[(1'-N-methylamino)ethyl] pyrrolidine according to claim 1, wherein the complex formed from bidentate phosphine and ruthenium comprises a complex represented by the following general formula (11):

$$Ru(OCOR^{14})_2(L) \qquad (11)$$

wherein L is as defined in claim 1 and $R^{14}$ represents a $C_1$ to $C_4$ lower alkyl group or a trifluoromethyl group.

4. The process for producing (3R,1'S)-1-benzyl-3-[(1'-N-methylamino)ethyl]pyrrolidine according to claim 1, wherein the complex formed from bidentate phosphine and ruthenium comprises a complex represented by the following general formula (12):

$$RuX_2(L) \qquad (12)$$

wherein L is as defined in claim 1 and X represents a halogen atom.

5. The process for producing (3R,1'S)-1-benzyl-3-[(1'-N-methylamino)ethyl]pyrrolidine according to claim 1, wherein the complex formed from bidentate phosphine and ruthenium comprises a complex represented by the following general formula (13):

$$RuX_kJ_m(L)Q_n \qquad (13)$$

wherein L is as defined in claim 1, X represents a halogen atom, and J represents benzene, p-cymene, a $C_1$ to $C_4$ lower alkyl benzoate or acetonitrile, and Q represents a halogen atom, $ClO_4$, $PF_6$ or $BF_4$; wherein J is benzene, p-cymene or a lower alkyl benzoate, m is 1, n is 1 and k is 1; or wherein J is acetonitrile, m is 1, n is 1 and k is 1, or wherein m is 4, n is 2 and k is 0.

6. The process for producing (3R,1'S)-1-benzyl-3-[(1'-N-methylamino)ethyl]pyrrolidine according to claim 1, which comprises reducing (3S,1'R)-1-benzyl-3-[(1'-hydroxy) ethyl]-2-pyrrolidinone represented by formula (2) with lithium aluminum hydride, borane, sodium borohydride and sulfuric acid or with sodium borohydride and a Lewis acid.

7. The process for producing (3R,1'S)-1-benzyl-3-[(1'-N-methylamino)ethyl]pyrrolidine according to claim 1, which comprises reacting (3R,1'R)-1-benzyl-3-[(1'-hydroxy)ethyl] pyrrolidine represented by formula (3) with methanesulfonyl chloride or paratoluenesulfonyl chloride in the presence of a base.

8. The process for producing (3R,1'S)-1-benzyl-3-[(1'-N-methylamino)ethyl]pyrrolidine according to claim 1, which comprises reacting (3R,1'R)-1-benzyl-3-[(1'-methanesulfonyloxy)ethyl]pyrrolidine and/or (3R,1'R)-1-benzyl-3-[(1'-paratoluenesulfonyloxy)ethyl]pyrrolidine represented by formula (4) with methylamine in an organic solvent.

* * * * *